United States Patent [19]

Kaplan et al.

[11] Patent Number: 4,754,030

[45] Date of Patent: Jun. 28, 1988

[54] CEFBUPERAZONE CRYSTALLINE TRIETHYLAMINE SALT

[75] Inventors: Murray A. Kaplan, Syracuse; Robert A. Lipper, Manlius, both of N.Y.

[73] Assignee: Bristol-Myers Company, New York, N.Y.

[21] Appl. No.: 697,172

[22] Filed: Feb. 1, 1985

[51] Int. Cl.[4] .................. C07D 501/36; A61K 31/545
[52] U.S. Cl. .................................................... 540/221
[58] Field of Search ..................... 544/20, 27; 540/221

[56] References Cited

U.S. PATENT DOCUMENTS 4,160,863  7/1979  Bowzard et al. ..................... 544/20
4,263,292  4/1981  Saikawa et al. ....................... 544/20

FOREIGN PATENT DOCUMENTS 1104938  3/1968  United Kingdom ................. 544/20

*Primary Examiner*—Donald G. Daus
*Assistant Examiner*—William A. Teoli, Jr.
*Attorney, Agent, or Firm*—R. E. Carnahan

[57] ABSTRACT

The crystalline triethylamine salt of cefbuperazone is stable in the dry state and soluble in water and in aqueous injection vehicles.

1 Claim, 1 Drawing Sheet

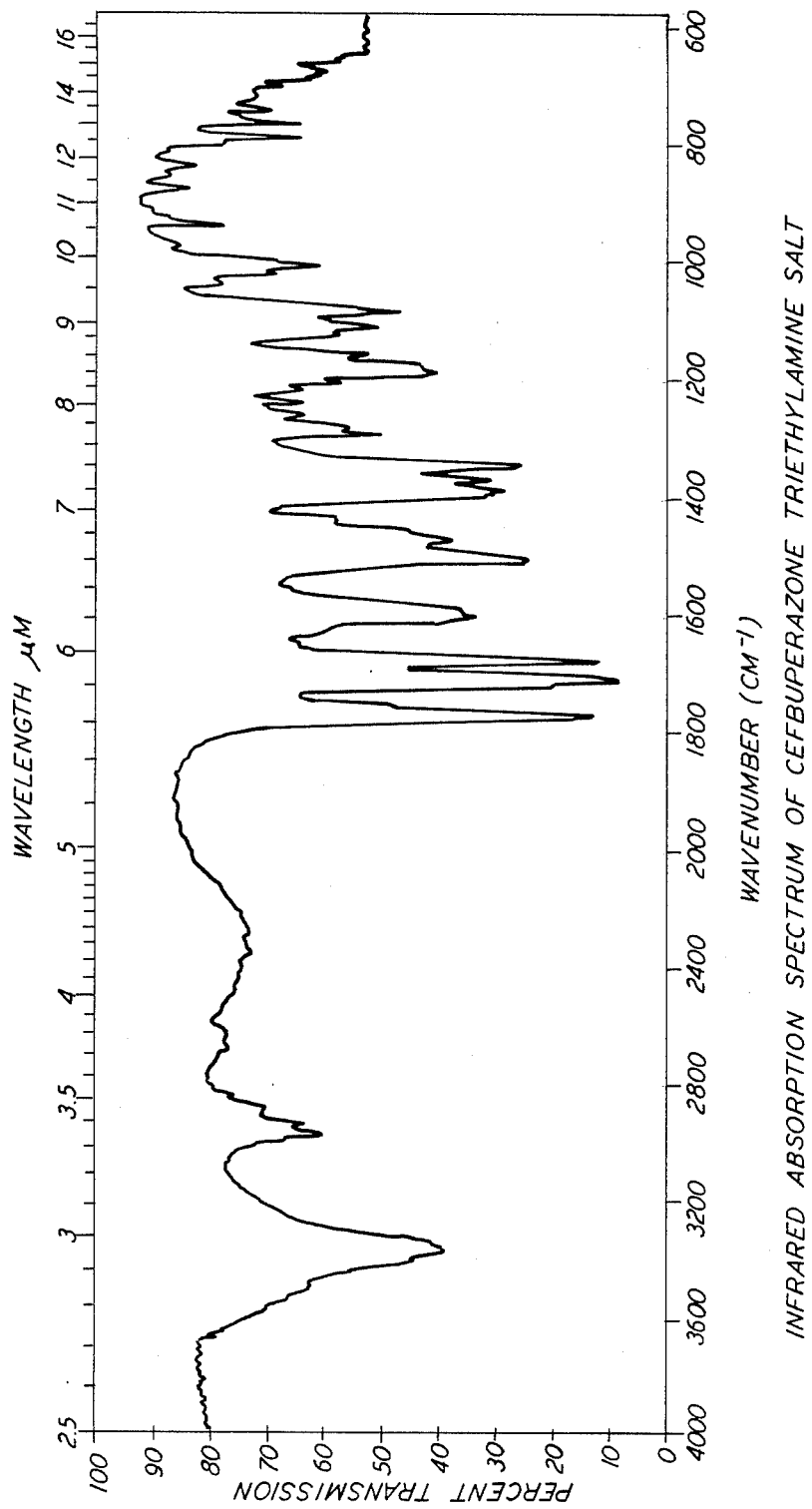

CEFBUPERAZONE CRYSTALLINE TRIETHYLAMINE SALT

FIELD OF THE INVENTION

The present invention refers to the stable crystalline triethylamine salt of cefbuperazone, a cephalosporin antibiotic (Class 424, Subclass 246).

DESCRIPTION OF THE PRIOR ART

Cefbuperazone is a so-called second generation injectable cephalosporin which has the following structure and is the subject of U.S. Pat. No. 4,263,292 patented Apr. 21, 1981.

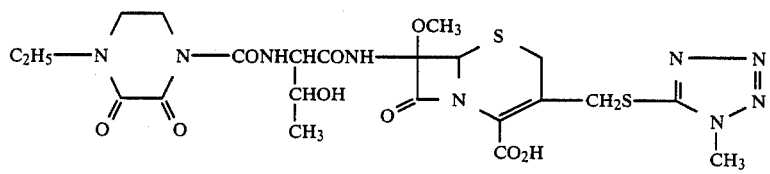

The sodium salt of cefbuperazone is under clinical development in Japan by Toyama Chemical Co., Ltd.

The foregoing patent, at column 30, describes injectable pharmaceutical preparations employing the sodium salt of cefbuperazone which is prepared by a freeze-dry process. The sodium salt is employed because the free acid form of the antibiotic is insoluble in water. The only crystalline form of the antibiotic described in the patent is the dihydrate of the free acid form. The dihydrate is unsatisfactory, or at least inconvenient for use in pharmaceutical products because the water of hydration is very loosely held and the composition of the preparation, while remaining crystalline, varies with the ambient conditions. The lyophilized sodium salt likewise is less than optimal with respect to pharmaceutical properties since in the dry state it lacks sufficient stability for long term storage, that is for periods in excess of one year. Accordingly, a need exists for an improved form of cefbuperazone for pharmaceutical formulation purposes and as a form suitable for bulk storage as an intermediary in manufacturing operations. The generic description of the family of cephalosporins referred to in the foregoing patent includes at column 4, line 61, mention of triethylamine salts, but no specific triethylamine salt is described nor are the attributes of the present salt alluded to.

SUMMARY OF THE INVENTION

In addressing the foregoing problem, applicants have prepared and examined the sodium, potassium, calcium, and ammonium salts of cefbuperazone and in addition salts prepared from cefbuperazone and the following bases: lidocaine, ethanolamine, triethanolamine, tris(hydroxymethyl)aminomethane, nicotinamide, ethylenediamine, N-methylglucamine, L(+)-lysine, and (L+)-arginine. None of these substances yielded a crystalline product, and none of the amorphous materials resulting offered any advantage with respect to stability in the dry state over the lyophilized sodium salt. Triethylamine among all the bases tested was the only one which yielded a crystalline salt and this only when prepared according to the process of the present invention.

The following table contains stability data from tests conducted on the particular salt forms of cefbuperazone indicated in the table. The crystalline-TEA (triethylamine) salt was prepared as described below. The amorphous-Na were prepared by a lyophilization process substantially as disclosed in U.S. Pat. No. 4,263,292. The amorphous-TEA salt was prepared by lyophilization of an aqueous solution thereof have pH 6.0, and prepared from the antibiotic and 1.1 molar proportions of triethylamine.

| | Stability of Crystalline and Amorphous Forms of Various Salts | | | | | | | | |
|---|---|---|---|---|---|---|---|---|---|
| | % Loss | | | | | | | | |
| | 45° C. (weeks) | | | 56° C. (weeks) | | | 70° C. (days) | | | 37° C. |
| Salt Form | (2) | (4) | (8) | (1) | (2) | (4) | (1) | (2) | (3) | 4 months |
| Crystalline-TEA | 2.8 | 2.6 | 2.8 | 2.9 | 2.6 | 2.6 | 0 | 0.8 | 2.0 | 0 |
| Amorphous-TEA | 12.0 | — | — | 20.5 | — | — | 13.5 | 20.5 | 23.7 | — |
| Amorphous-Na | 27.0 | — | — | — | 32.0 | — | 6.0 | — | 26.2 | — |

It is evident that the crystalline triethylamine salt exhibits highly satisfactory stability characteristics when stored in the dry state. No loss was observed when stored for 4 months at 37° C. At 45° C. the loss in activity during 2 weeks storage for the crystalline triethylamine salt was 2.8% as compared to 12% for the amorphous triethylamine salt and 27% for the amorphous sodium salt. During a total of 8 weeks storage at this temperature, the crystalline-TEA salt suffered no further loss. Similarly at 56° C. for 1 week, there was a 2.9% loss in antibiotic activity for the crystalline triethylamine salt, but a 20.5% loss for the amorphous triethylamine salt and a 32% loss after 2 weeks with the amorphous sodium salt. During the 4 week test period no additional loss in activity from the crystalline triethylamine salt was observed. At 70° C. after 3 days a 2% loss in activity of the crystalline triethylamine salt had occurred while 23.7% and 26.2% losses were observed respectively for the amorphous triethylamine salt and the amorphous sodium salt.

The crystalline salt of the present invention has been characterized by elemental analysis, melting point determined with a differential scanning calorimeter, X-ray powder diffraction pattern, and infra-red spectrum. In the nuclear magnetic resonance spectrum, chemical shifts, characteristic of the cefbuperazone $CH_3$ protons are obscured by the triethylamine. The data with respect thereto appear herein.

The intraperitoneal $LD_{50}$ for the crystalline cefbuperazone-TEA determined in mice is approximately 2,000 mg per kg. This is a somewhat lower value than that of the amorphous sodium salt. The $LD_{50}$ of the latter was not determined, but no deaths were observed in a group of 10 mice treated intraperitoneally with 2,000 mg per kg thereof. Similarly, the intracranial toxicity in mice of cefbuperazone crystalline triethylamine salt is $LD_{50}=280$ mg/kg. The freeze-dried sodium salt of cefbuperazone in the same test fails to reflect any toxicity at 400 mg/kg. These results are believed to reflect a low level of toxicity comparable to that of penicillin-G.

DESCRIPTION OF SPECIFIC EMBODIMENTS

A critical feature in the preparation of the crystalline triethylamine salt of the present invention is the use of methylene chloride or of methylene chloride containing up to 10% by volume of a $CH_2Cl_2$-miscible water soluble oxygenated organic solvent as the reaction medium. Suitable oxygenated organic solvents include ethyl acetate, acetone, tetrahydrofuran, and a lower alkanol such as ethanol, isopropanol, or butanol. Methanol may be employed, but this solvent has an inclination to rupture the beta-lactam ring by a solvolytic process and it is desirable to avoid contact with methanol. The salt forms on contact of the ingredients at room temperature, 20°-25° C. and may be recovered by diluting the reaction mixture with a further quantity of the oxygenated organic solvent provided the salt is insoluble in that solvent. We prefer to use acetone as the oxygenated organic solvent. If desired, aseptic filtration of the reaction solution may be employed for sterilization and purification purposes and if aseptic technique is used for the crystallization step using the oxygenated organic solvent, material suitable for parenteral formulations may be produced. This is illustrated in the following procedure.

PREPARATION OF CRYSTALLINE, STABLE TRIETHYLAMINE SALT

Mix 10 g of cefbuperazone with a mixture of 40.0 ml of methylene chloride and 4.0 ml of acetone at 20°-25° C. under dry nitrogen. Add 2.2 ml of triethylamine (1.05 molar equivalent) with very rapid stirring over a 5 minute interval. A solution containing a slight haze is obtained. Using aseptic technique, pass the solution through an appropriate, sterile, 0.22 micron pore size membrane filter. Collect the filtrate in a suitable, sterile container. With rapid stirring, add 200 ml of sterile acetone over a 15 minute interval. Crystals form. Continue stirring for 10 minutes. Add 200 ml of sterile acetone over a 15 minute interval. Stir for 0.5 hour. Using aseptic procedures, collect the crystals by vacuum filtration. Wash the crystals with 2×40 ml portions of sterile acetone. High vacuum dry the crystals at aseptic conditions for 24 hours at 40°-45° C. Collect and store the crystals in a sterile glass container. Expected yield: 9.2 g of triethylamine cefbuperazone salt, m.p. 160°-163°.

The form of cefbuperazone used as starting material in the foregoing procedure is not critical. The dihydrate described in U.S. Pat. No. 4,263,292 is quite satisfactory, but dehydrated material may be used without any advantage.

The elemental analysis of this material is indicated below:

|  | Found | Dry Basis | Theory* |
|---|---|---|---|
| % $H_2O$, KF | 0.41 | — | — |
| % C | 46.3 | 46.48 | 46.14 |
| % H | 6.16 | — | 6.0 |
| % N | 18.76 | 18.78 | 19.2 |
| % S | 7.96,8.39 | 7.96,8.41 | 8.8 |

*Calc'd. for" $C_{22}H_{29}H_9O_9S_2.C_6H_{15}N$

The infra-red absorption spectrum prepared using a pelletized KBr dilution of the crystalline material is illustrated in FIG. 1 hereof.

The NMR spectrum is as follows: δ, ppm ($D_2O$, TSP as reference): 5.16 (singlet, integral 1); 4.08 (singlet, integral 3); 3.58 (singlet, integral 3); 4.2-4.4 (quartet, J ca 7 Hz), integral 6); and 1.0-1.5 (overlap patterns, integral 15).

The X-ray powder diffraction pattern was determined on a Rigaku X-Ray Powder Diffractometer using a Cu 25 kv lamp operated at 20 ma, at a scan rate of 2° per minute from 40° to 5° using a chart speed of 10 mm per minute and a nickel filter. The d-spacings calculated from these measurements are listed below. The relative intensities were estimated by measurement of the peak heights on a tracing corresponding to the d-spacings.

| d-Spacing (Å) | Estimated Relative Intensity (%) |
|---|---|
| 9.2 | 66.7 |
| 8.18 | 14.3 |
| 6.96 | 33.3 |
| 6.70 | 55.6 |
| 5.70 | 17.5 |
| 4.82 | 63.5 |
| 4.07 | 100.0 |
| 3.97 | 27.0 |
| 3.67 | 14.3 |
| 3.63 | 15.9 |
| 3.24 | 17.5 |

Solubility

The crystalline cefbuperazone-TEA salt of this invention is soluble in water in a wide range of proportions. It readily dissolves in the common injection vehicles including water, 5% glucose, and saline. It is substantially insoluble in the common organic solvents except methylene chloride and similar halogenated lower alkanes.

We claim:

1. The crystalline triethylamine salt of cefbuperazone which exhibits mp 160°-163° C., has the elemental composition corresponding to the formula $C_{22}H_{29}N_9O_9S_2.C_6H_{15}N$ and exhibits substantially the X-Ray powder diffraction pattern described below determined with a Rigaku X-Ray Powder Diffractometer operated with a Cu 25 kv lamp and a nickel filter at a scan rate of 2° per minute over the range of from 40° to 5°.

| d-Spacing (Å) | Estimated Relative Intensity (%) |
|---|---|
| 9.2 | 66.7 |
| 8.18 | 14.3 |
| 6.96 | 33.3 |
| 6.70 | 55.6 |
| 5.70 | 17.5 |
| 4.82 | 63.5 |
| 4.07 | 100.0 |
| 3.97 | 27.0 |
| 3.67 | 14.3 |
| 3.63 | 15.9 |
| 3.24 | 17.5 |

* * * * *